United States Patent [19]
Malec et al.

[11] Patent Number: 5,279,416
[45] Date of Patent: Jan. 18, 1994

[54] LIGATING DEVICE CARTRIDGE WITH SEPARABLE RETAINER

[75] Inventors: Richard M. Malec, Durham; John C. Phillips, Holly Springs; Curtis W. Thornton, Cary; Elise Powell, Raleigh, all of N.C.

[73] Assignee: Edward Weck Incorporated, Research Triangle Park, N.C.

[21] Appl. No.: 893,867

[22] Filed: Jun. 5, 1992

[51] Int. Cl.$^5$ .............................................. B65D 85/24
[52] U.S. Cl. ................................... 206/339; 206/63.3; 206/341
[58] Field of Search ......................... 206/63.3, 339-341

[56] References Cited

U.S. PATENT DOCUMENTS

| | | |
|---|---|---|
| 3,270,745 | 9/1966 | Wood . |
| 3,326,216 | 6/1967 | Wood . |
| 3,351,191 | 11/1967 | Mallina . |
| 3,363,628 | 1/1968 | Wood . |
| 3,439,522 | 4/1969 | Wood . |
| 3,439,523 | 4/1969 | Wood . |
| 3,631,707 | 1/1972 | Miller . |
| 3,713,533 | 1/1973 | Reimels . |
| 4,076,120 | 2/1978 | Carroll et al. . |
| 4,146,130 | 3/1979 | Samuels et al. . |
| 4,212,390 | 7/1980 | Raczkowski et al. . |
| 4,294,355 | 10/1981 | Jewusiak et al. . |
| 4,344,531 | 8/1982 | Gjersch . |
| 4,361,229 | 11/1982 | Mericle . |
| 4,412,617 | 11/1983 | Cerwin . |
| 4,619,262 | 10/1986 | Taylor . |
| 4,685,564 | 8/1987 | Hills et al. . |
| 4,696,396 | 9/1987 | Samuels . |
| 4,834,096 | 5/1989 | Oh et al. . |
| 4,936,447 | 6/1990 | Peiffer . |
| 4,961,499 | 10/1990 | Kulp . |
| 4,972,949 | 11/1990 | Peiffer . |
| 5,026,382 | 6/1991 | Peiffer . |
| 5,046,611 | 9/1991 | Oh ...................................... 206/339 |

FOREIGN PATENT DOCUMENTS 1309342 3/1973 United Kingdom .

Primary Examiner—Bryon P. Gehman
Attorney, Agent, or Firm—Gene Warzecha

[57] ABSTRACT

A cartridge for storing and retaining a plurality of medical ligating devices such as hemostatic clips and surgical staples, the cartridge having a movable device retaining member situated in each device chamber. The retaining member is adapted to frictionally engage the legs of an open C-shaped device and is further adapted to be displaced away from engagement with the device when it is engaged in the jaws of a forceps-type applier. In one embodiment, the retaining member is adapted to fit between the legs of an open hemostatic clip and is further adapted to be displaced downwardly away from the clip when the clip is engaged by a clip applier. The disclosure further includes a method of storing hemostatic clips in a cartridge, the method incorporating retaining the clip within the cartridge by a separable member which is displaceable from engagement with a clip when the clip is engaged by a clip applier.

13 Claims, 19 Drawing Sheets

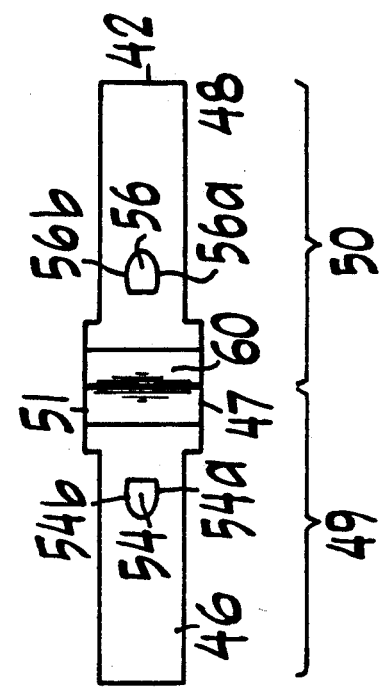
FIG. 10
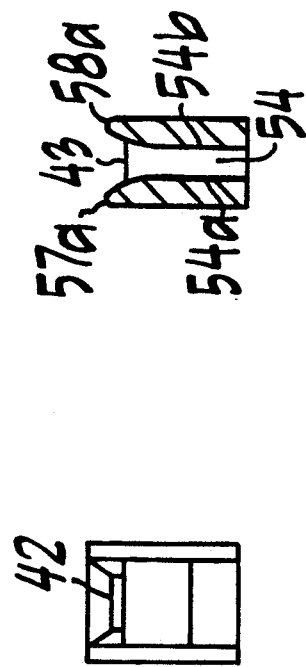
FIG. 12
FIG. 11
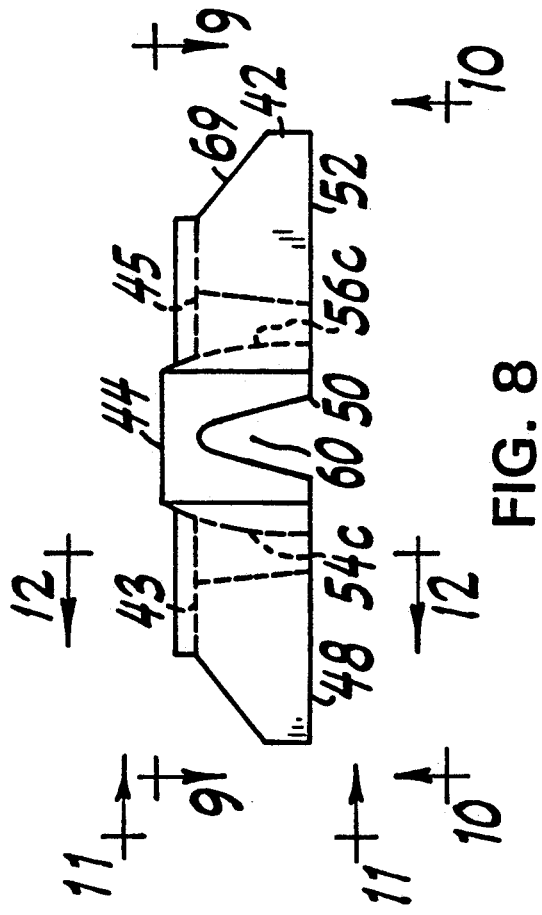
FIG. 8
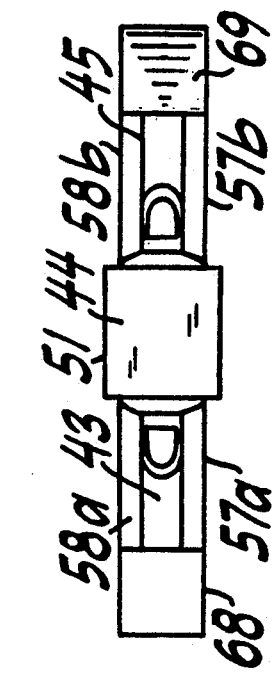
FIG. 9

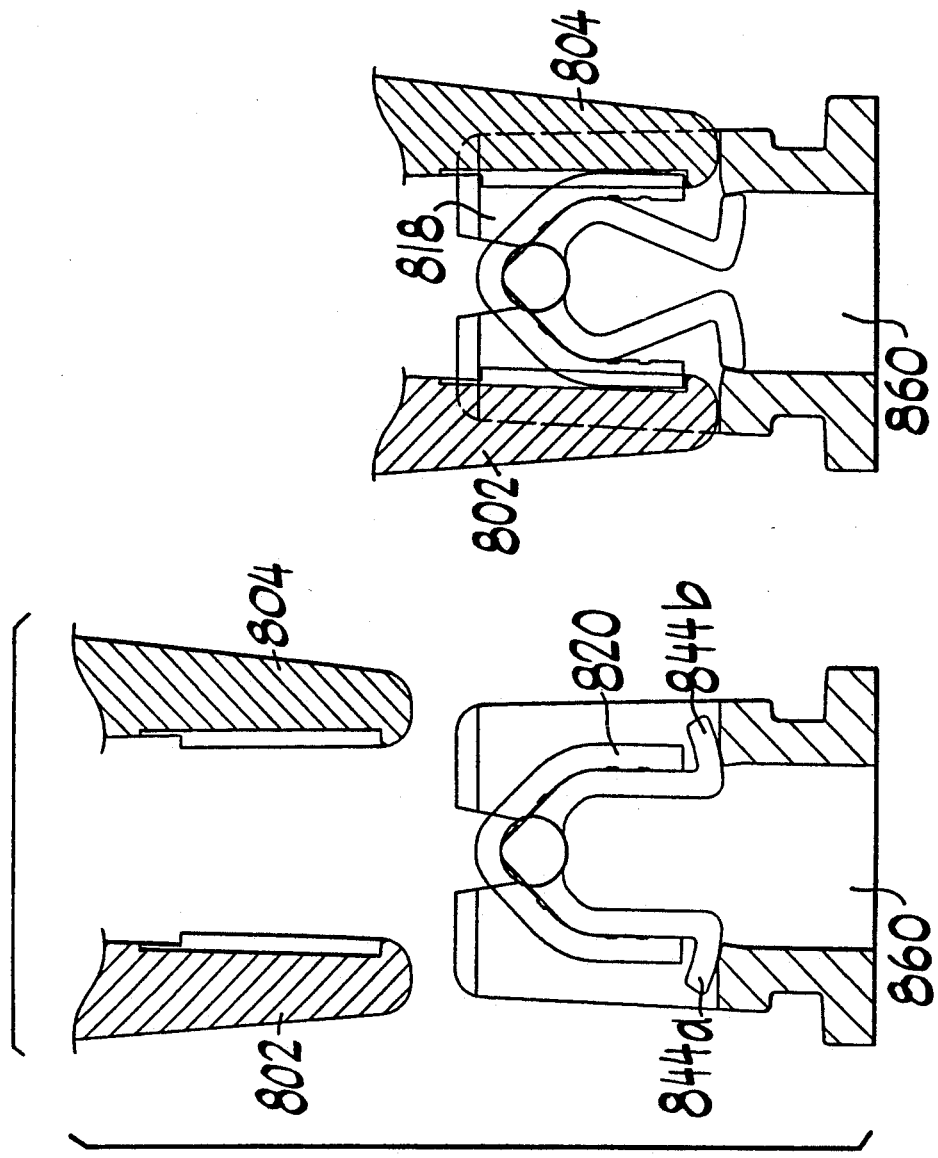
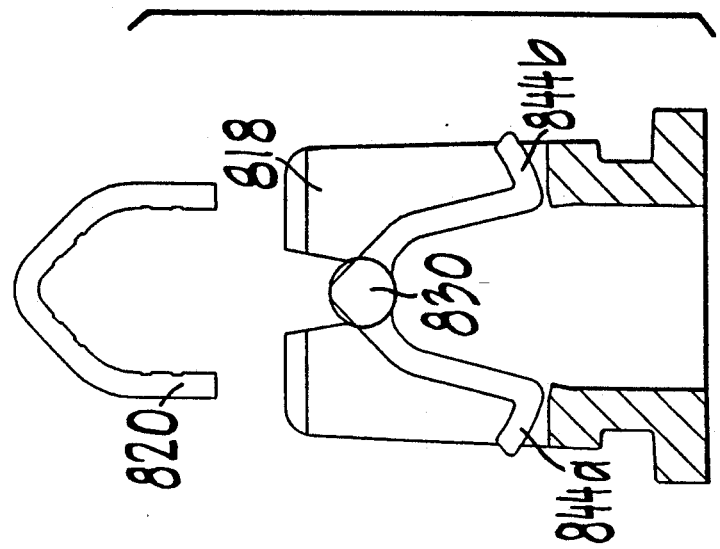
FIG. 33
FIG. 32
FIG. 31

LIGATING DEVICE CARTRIDGE WITH SEPARABLE RETAINER

BACKGROUND OF THE INVENTION

1. Field of the Invention

The invention relates generally to holders for storing and retaining ligating devices such as surgical staples and hemostatic clips prior to use. More particularly, the invention relates to cartridges which facilitate the storage and retention of a plurality of ligating devices within a corresponding plurality of individual chambers of the cartridge prior to withdrawal of the devices by a forceps-type applier.

2. Description of the Prior Art

Hemostatic or ligating clips have long been used to ligate or clamp blood vessels during surgical procedures. The terms "hemostatic" and "ligating" are interchangeably used herein to mean any clips which squeeze tissue to effect a blockage. While the clips are usually integrally formed, in some applications such as aneurysm clips the devices are formed of more than one piece. The clips are generally made of either a biocompatible metallic material or of a polymeric or non-metallic material. While it is convenient to describe the invention in terms of hemostatic clips, to the extent that staples and clips are similar medical devices it will be understood that the present invention is adaptable for use with ligating devices such as surgical staples. For ease of explanation, the term "clips" will be used herein but this should be understood to encompass "staples" as well.

In general, the clips are C-shaped, U-shaped or V-shaped when in their open configuration and are designed such that the opposing legs of the open clip are able to be closed together by being compressed by the jaws of a forceps-type clip applier. In the case of surgical staples the staple profile may be a slight variation of an open "C", "V" or "U". For example, one type of staple adaptable for use with the present invention is shown in U.S. Pat. No. 4,375,866 (Giersch et al.), assigned to the assignee hereof and incorporated by reference herein. In the case of metallic clips, the material is sufficiently strong such that the clips remain in their crimped, closed position merely by squeezing the legs together. In the case of plastic-type clips, the material is not as strong and requires some auxiliary latching mechanism to keep the clips closed. For the foregoing reasons, metallic clips are generally symmetrical while plastic clips are not. The latching mechanism of the latter generally comprises a hook-type arrangement molded with or otherwise secured to the plastic clip. One example of such a plastic ligating clip is shown in U.S. Pat. No. 4,834,096 (Oh et al.) assigned to the assignee hereof.

Because hemostatic clips are small and because many clips are usually used in a surgical procedure, holding devices or cartridges are used to store and retain the clips—whether metallic or plastic—between the time of their manufacture and their ultimate use in a surgical procedure. While numerous clip cartridges are known, they all serve to prevent the clips from becoming loosened during shipment and handling and from becoming completely dislodged. A distinction should be made between clip cartridges intended for use with "manual" clip appliers and those intended for use with "automatic" clip appliers. As used herein, the term "automatic" means those clip appliers which retain a plurality of hemostatic clips adjacent the jaws of a clip applier in a way such that a new clip is automatically fed to the jaws after the previous clip has been crimped into place. As used herein, the term "manual" means clip appliers which receive one clip at a time between the jaws and which have to be reloaded manually after the previous clip is crimped. The reloading operation is generally accomplished by inserting the jaws of the applier into a clip holder or cartridge which is generally provided with a plurality of longitudinally spaced, clip retaining chambers. A single clip is retained in each chamber by a variety of means, legs facing downwardly, and is removed from its chamber by a forceps-type clip applier which is inserted into each clip chamber and secured to the clip sufficiently to overcome whatever clip retention means is utilized to enable the clip to be removed from the clip chamber. The jaws of the clip applier generally have longitudinal grooves to receive the clip legs and may have end-dams at the distal end of each groove to limit distal movement of the clip. The clip is secured in the jaws by the natural resiliency of the clip legs and by the end-dams if they are present.

Various mechanisms are known by which clips may be retained within the chambers of clip cartridges for use with manual clip appliers. In all instances, a desirable goal of such cartridges is to minimize the forces required to load the clip into the applier and to then remove it from the cartridge while maximizing the security with which the clip is held in the cartridge and, subsequently, the applier jaws prior to use. With respect to metallic clips in manual clip cartridges, friction between the clip and other surfaces within its individual chamber is generally sufficient to retain the clip. Cartridges may be categorized according to the surfaces by which the frictional forces are applied to the clip: side wall, end wall or central post.

The clip cartridges are generally made of molded plastic material (for example, polycarbonate or polyphenoline oxide) such that the walls of each clip chamber are somewhat resilient. Consequently, with respect to side wall type cartridges designed to hold clips by frictional engagement with the side walls, the latter are sometimes able to be pushed away from each other (longitudinally) when the clip applier jaws are inserted into the chamber to retrieve the clip. Examples of cartridges holding the clips in their respective clip chambers by means of frictional engagement with the side walls of each chamber is shown in U.S. Pat. No. 4,076,120 (Carroll et al.) and U.S. Pat. No. 4,961,499 (Kulp). Another type of known prior art side wall cartridge has a plurality of ribs extending longitudinally from each side wall of each clip chamber inwardly toward the clip to retain the clip by frictional engagement with the ribs (U.S. Pat. No. 4,696,396, Samuels). However, such configurations result in frictional contact between the side walls and the applier, thus resulting in some force being required to remove the loaded applier. Prior to the subject invention, all side wall type cartridges required some force to be applied to the applier to remove it and the clip from the cartridge.

In some prior art clip cartridges, each individual clip chamber is provided with a central post generally conforming to the shape of the open clip although being slightly larger so that when the clip is pushed onto the central post the legs are spread slightly so that frictional contact between the legs of the clip and the central post retains the clip within its chamber. Cartridges of this "central post" type are shown in U.S. Pat. Nos. 3,270,745, 3,326,216, 3,363,628, 3,439,522 and 3,439,523, all issued to E. C. Wood. While such cartridges serve to securely retain clips, the friction required to retain the clips in the cartridges also makes it more difficult to load the clips into the jaws of a clip applier and to then remove the clip from the cartridge. As the jaws are pushed down onto the clip the central post keeps the clip legs from closing, thereby forcing the jaws away from each other. If the jaws merely have a groove to receive the clip legs, the frictional force between the jaws and the clip must be greater than that between the clip legs and the post in order for the clip to be removed. If the jaws have an end-dam at the distal tip of each groove, the clip may be more easily removed from central-post type cartridges (and others) because the end-dams act directly on the clip legs with whatever upward removal force is applied to the applier. However, in situations where the clip is roughened or coated to enhance its tissue gripping ability, the frictional contact between the clip legs and the post is even greater than normal and, consequently, an even greater removal force is required. An example of such clips is disclosed in copending U.S. patent application Ser. No. 07/790,104 assigned to the assignee hereof and incorporated by reference herein. Even if the clips are not coated or roughened, the frictional contact between the post and the clip may be sufficient to leave a residue of particulate matter caused by the clip shaving the post. Minimizing the amount of this particulate is an object of this invention.

In order to minimize the forces associated with clip removal some prior art cartridges retain unformed clips (i.e. clips in a partially straightened state) by maintaining each clip under tension within its chamber by the interaction between the central post in the chamber, the central (hinge) part of the clip and protrusions extending transversely into each chamber toward the central post. These are termed end-wall type cartridges. Each clip is retained in its chamber by having its central hinge part pushed upwardly by the central post and its ends pushed downwardly by the protrusions. Such a cartridge is shown in U.S. Pat. No. 3,713,533 (Reimels) and U.S. Pat. No. 4,146,130 (Samuels et al.)

The aforementioned U.S. Pat. No. 4,146,130 (Samuels et al.) shows an alternative embodiment for the situation where clips ar intended to be loosely maintained in the cartridge without frictional engagement between it and the chamber, the clips in such an event being retained in each cartridge by a covering tape which may be easily severed by the applier as desired. However, it is generally not desirable to have metallic clips too loosely held within clip cartridges since the orientation of the clips is then subject to change. If the clips are not consistently held in a certain orientation, it is difficult to load the clips into clip appliers because the clip legs are not consistently aligned with the grooves of the applier jaws. Consequently, a force-balancing process has to be considered to produce a cartridge having sufficient clip holding or storage force and minimal (or zero) clip removing force.

Another end-wall type prior art clip cartridge is shown in U.S. Pat. Nos. 4,936,447 (Peiffer) and 4,972,949 (Peiffer) which shows a formed metallic clip being held within a clip compartment by being supported on a central post by a pair of inwardly extending transverse resilient fingers. The fingers are pushed downwardly by the distal tips of clip appliers so that as the clip legs are received in the grooves in the jaws in the clip applier the resilient fingers are pushed out of the way. With this device, since the grooves in the applier jaws do not have any end-dams, the clip must be slightly compressed as it is loaded into the jaws of the applier in order to produce enough frictional contact between the clip and jaws to prevent the clip from falling out. The Peiffer cartridge, however, is not suitable for use with clip appliers having end-dams since the end-dams would necessarily cause the clip legs to be compressed inwardly too much because there is nothing to support the legs to prevent closure. Therefore, when the dams clear the end of the clip leg the clip, having been compressed to a point where it does not have sufficient resiliency to firmly occupy the space between the grooves in the jaws, would not be securely retained within the jaws. While this device does offer low, desirable clip removal forces, the absence of end-dams in the jaws of the applier mandated by this device results in compromised clip security in the jaws.

It is an object of this invention to produce a clip cartridge for supporting metallic clips in a manner which minimizes the force with which the clip may be loaded into a forceps-type clip applier, minimizes the force with which the clip may be removed from the cartridge and is suitable for use with a clip applier having end-dams in the clip jaws or not having such end-dams.

It is an object of this invention to produce a hemostatic clip cartridge which minimizes the forces associated with the loading of clips into a forceps-type clip applier.

It is another object of this invention to provide a hemostatic clip cartridge for retaining clips during shipping and handling while enabling the withdrawal of the clips by clip appliers in preparation for use.

It is a further object of this invention to produce a hemostatic clip cartridge for storing and retaining a plurality of metallic hemostatic clips, prior to their subsequent removal by an associated clip applier, in a manner which minimizes the inward displacement of the clip legs during the loading of the clip into a forceps-type clip applier.

It is also an object of this invention to produce a clip cartridge for storing and retaining a plurality of hemostatic clips and for minimizing forces associated with the subsequent removal of a clip by an associated clip applier.

It is an additional object of this invention to produce a hemostatic clip cartridge of the side wall type in which frictional forces between the clip applier and the side walls are substantially reduced (if not eliminated) after the clip has been engaged in the applier jaws.

It is also an object of this invention to produce a clip cartridge for storing and retaining a plurality of hemostatic clips and for minimizing forces associated with the subsequent removal of a clip by an associated clip applier to such an extent that the loaded applier may be lifted from the cartridge without holding the cartridge down.

It is another object of this invention to produce a hemostatic clip cartridge suitable for storing and retaining a plurality of hemostatic clips which have been coated with a grip enhancing material and for minimizing forces associated with the subsequent removal of a clip by an associated clip applier.

It is yet another object of this invention to produce a cartridge for storing and retaining a plurality of generally C-shaped ligating devices (such as clips and staples) and for minimizing the forces required to remove the ligating devices by associated appliers.

SUMMARY OF THE INVENTION

These and other objects of this invention are achieved by the preferred embodiment of the invention disclosed herein which is embodied in a cartridge for holding hemostatic clips comprising a body provided with a plurality of clip chambers, each chamber for receiving a hemostatic clip. Each chamber is defined by a pair of walls generally parallel to the plane of the clip legs and is provided with a central support member which supports an open hemostatic clip. The clip is also retained in the chamber by frictional engagement with a clip retaining member adapted to fit between the legs of an open clip and under the central support member. The leg retaining member is movable out of engagement with the clip and out of position between the clip legs in response to downward pressure from a clip applier as it engages a clip. The walls of the clip chamber are far enough apart so as not to produce any significant frictional contact with the applier as it is lifted out of the cartridge.

The invention also comprises the method of retaining a clip within a clip cartridge. A clip cartridge is provided with a plurality of chambers for retaining clips, each chamber having a clip supporting member adapted to support the hinge portion of a clip. A clip retaining member is provided within each chamber, the clip retaining member being situated on the side of the clip supporting member opposite from the side which engages the clip. Each clip retaining member is sized so that when it is pressed into position between the legs of its corresponding clip the clip is securely held in the cartridge until the clip is engaged by a clip applier. When a user wants to remove a clip, a clip applier is positioned over the clip and pushed downwardly to engage the clip in the applier jaws. The downward motion displaces the clip retaining member downwardly as the clip is being engaged, thereby minimizing the force necessary to remove the clip from its chamber.

BRIEF DESCRIPTION OF THE DRAWINGS

FIG. 8 is a front elevational view of the clip retainer of the present invention.

FIG. 9 is a top plan view of FIG. 8 taken along the lines 9—9.

FIG. 10 is a bottom plan view of FIG. 8 taken along the lines 10—10.

FIG. 11 is an end view of FIG. 8 taken along the lines 11—11;

FIG. 12 is a sectional view of FIG. 8 taken along the lines 12—12.

FIG. 31 is a diagrammatic elevational view of a clip chamber of FIG. 30 before a clip is loaded.

FIG. 32 is a view of FIG. 31 after the clip has been loaded into the chamber.

FIG. 33 is a view of FIG. 32 after a clip applier has engaged the clip.

DESCRIPTION OF THE PREFERRED EMBODIMENT

Figure 1:
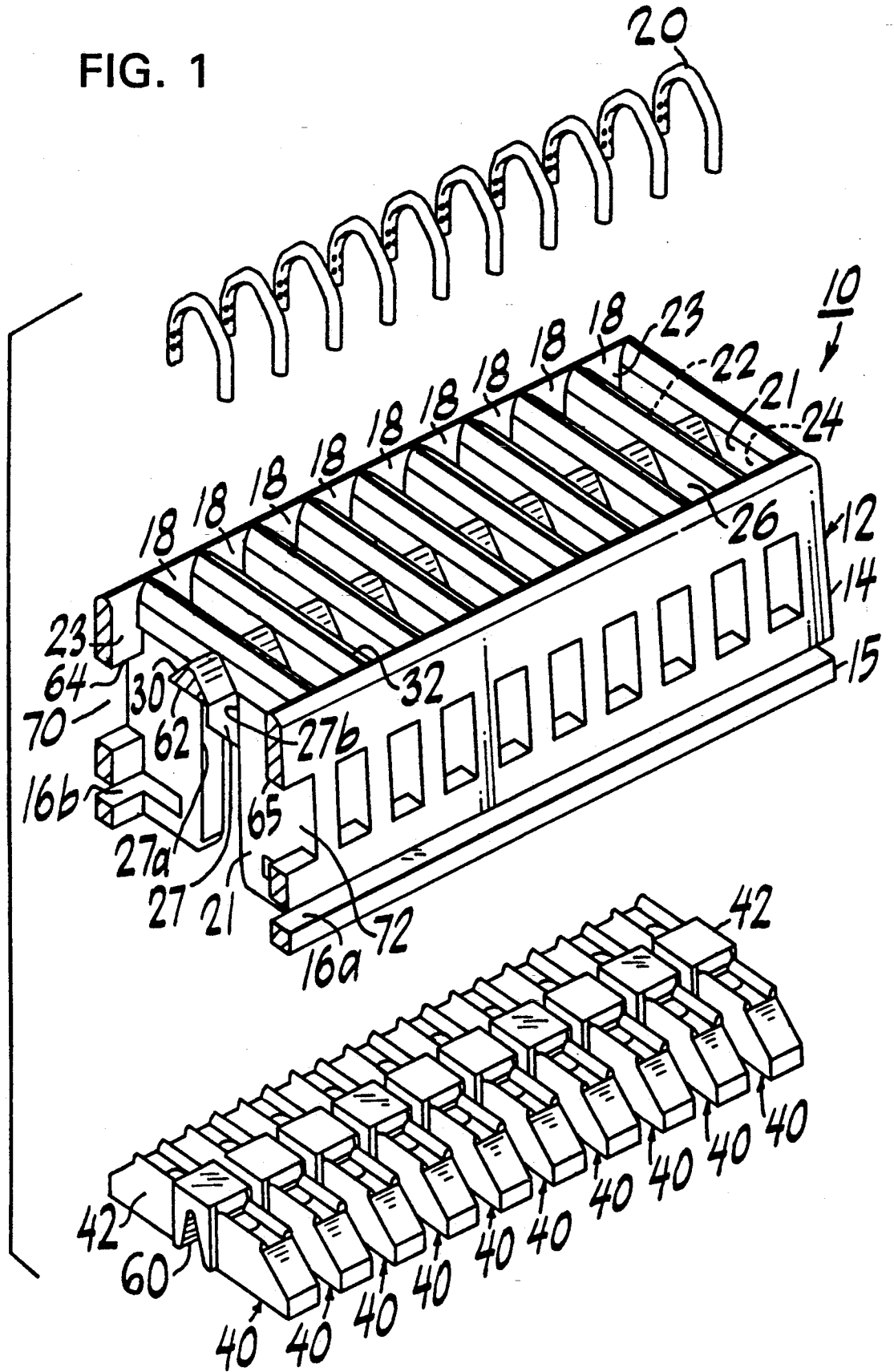
FIG. 1 is an exploded front perspective view of a clip cartridge constructed in accordance with the principles of this invention showing the components thereof.

Referring first to FIG. 1, there is shown an exploded perspective view of a clip cartridge 10 constructed in accordance with the principles of this invention.

Clip cartridge 10 has an integral body element 12 having a main body portion 14 and a base portion 15 spaced therefrom by a pair of parallel channels 16a and 16b. The latter facilitate securing the cartridge to a tray or other component during use. Body 14 is a longitudinally extending hollow body having a plurality of individual clip retaining chambers or compartments 18, each of which is identical and retains a clip 20.

Figure 5:
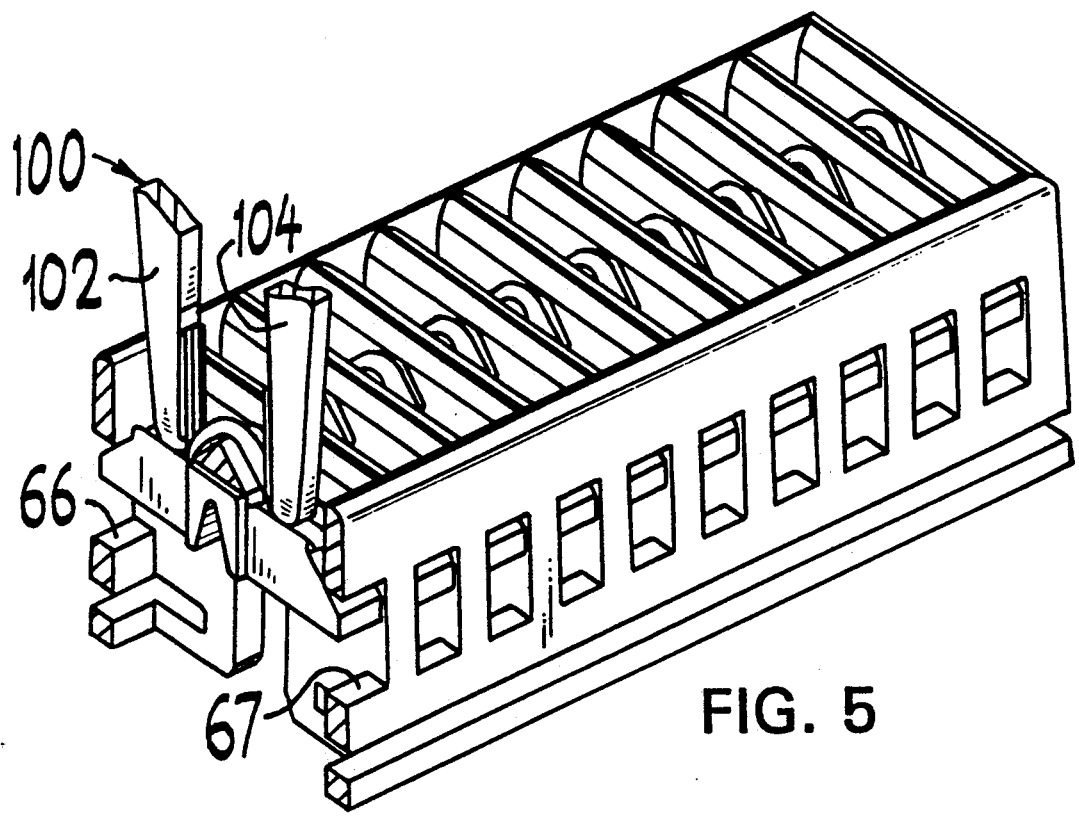
FIG. 5 is a front perspective, partially cut-away view of the cartridge of FIG. 1 and the jaws portion of a clip applier in place for use with the clips retained by the cartridge.
Figure 6:
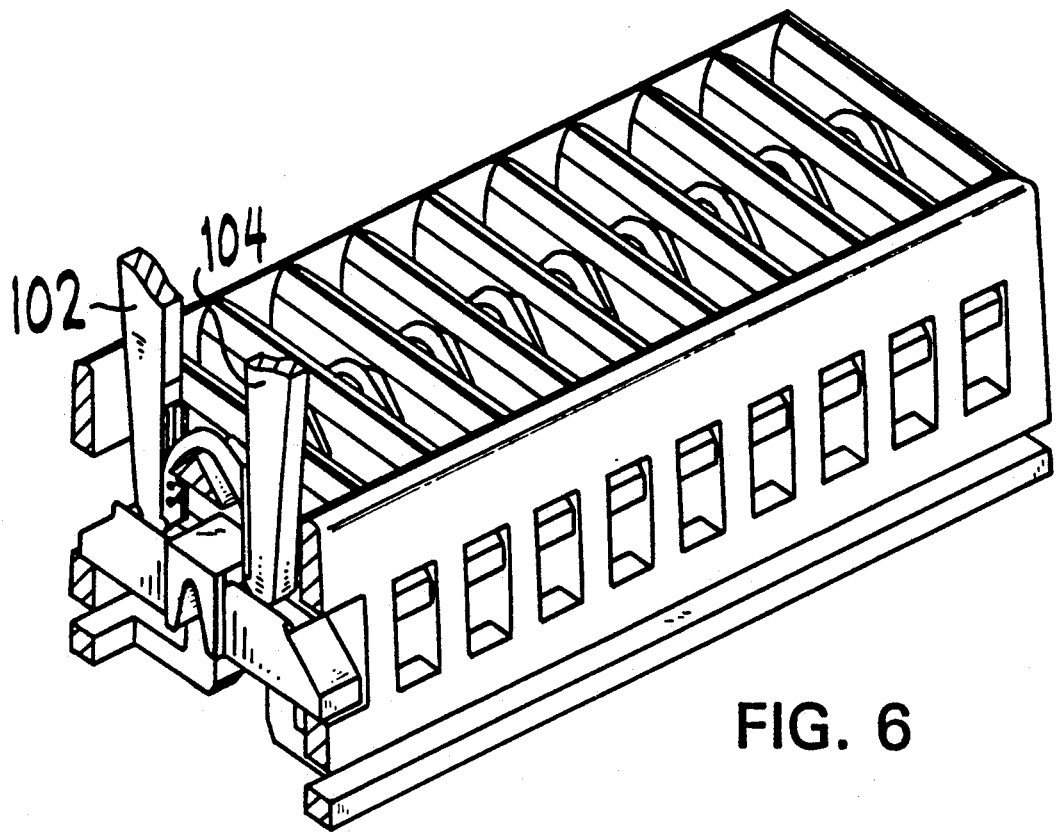
FIG. 6 is a view of FIG. 5 showing the clip applier after it has engaged a clip in the jaws of the applier.
Figure 7:
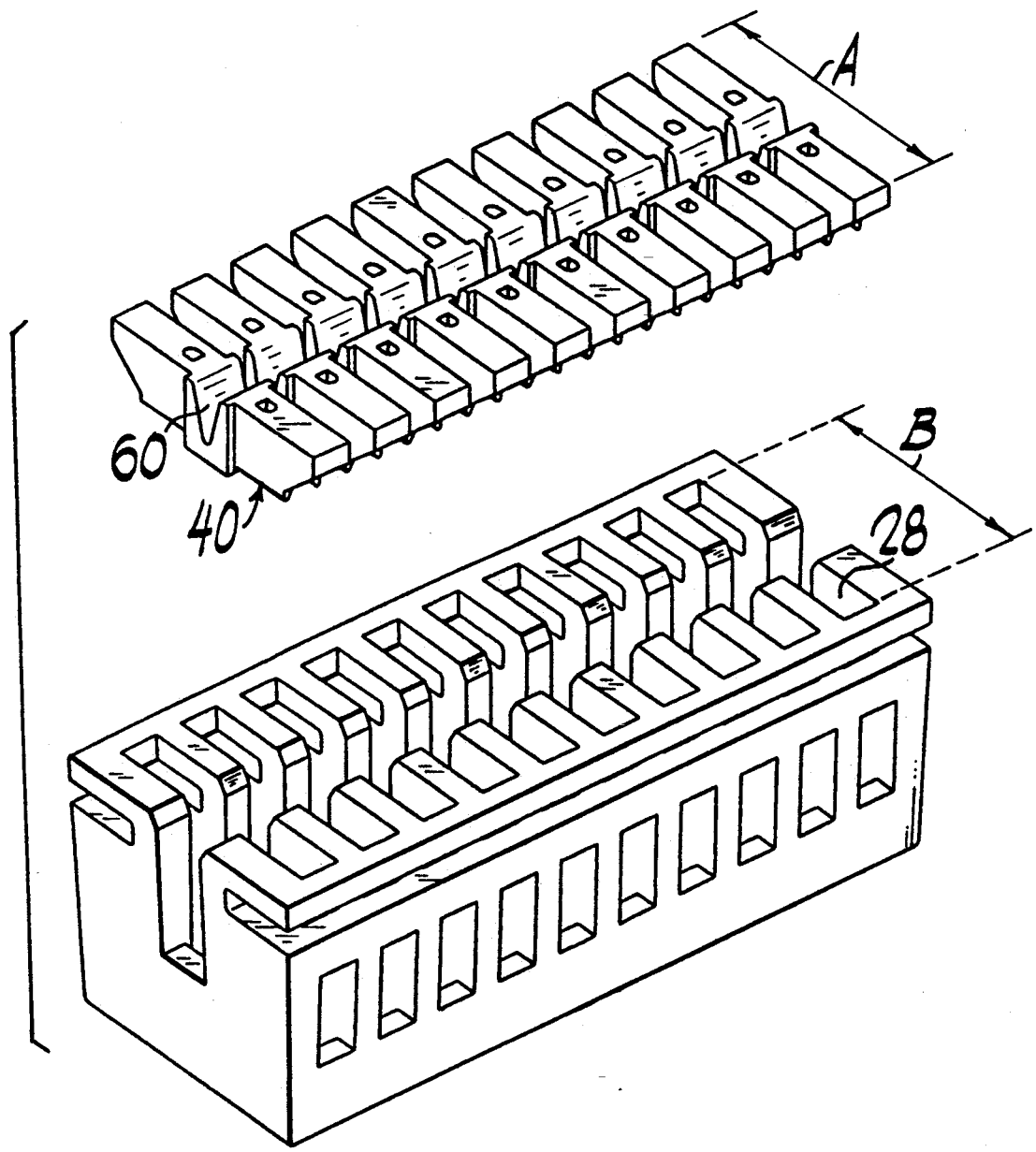
FIG. 7 is an exploded bottom perspective view of the cartridge of FIG. 1 (not showing clips).

Each clip chamber 18 is formed by parallel, longitudinally spaced transversely extending walls 32 having oppositely facing, transverse side surfaces 21 and 22, and longitudinally extending end walls 23 and 24. The end clip chambers 18 are bounded by walls 34 and 36. Each chamber 18 has an open top side 26, an open bottom side 28 (best seen in FIG. 7) and a central post 30. Posts 30 are integrally formed with walls 32 and have a V-shape to matingly fit into the hinge portion of a clip 20 (best seen in FIGS. 5 and 13). Since all clip chambers are identical, only one will be described in detail.

Figure 3:
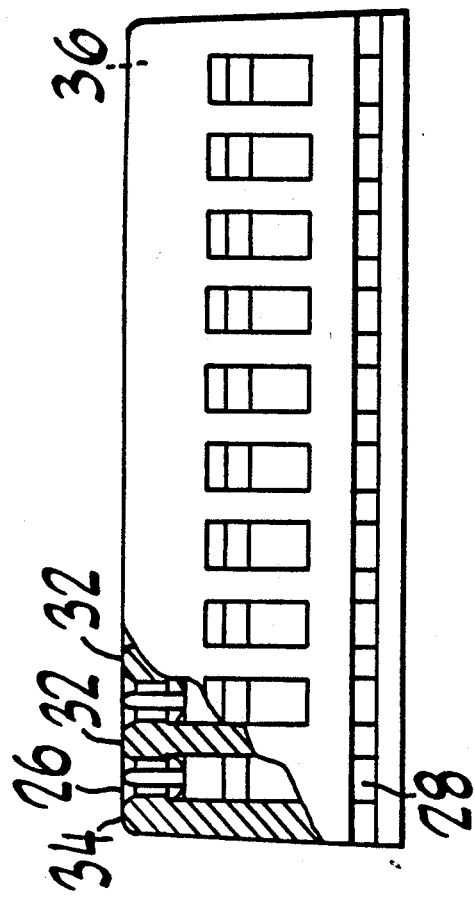
FIG. 3 is a side elevational view of FIG. 2, partially cut-away.
Figure 2:
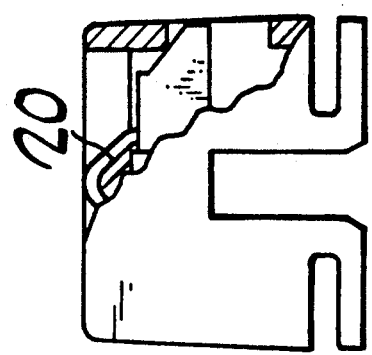
FIG. 2 is an end view of the cartridge of FIG. 1 in assembled form, partially cut-away.
Figure 14A:
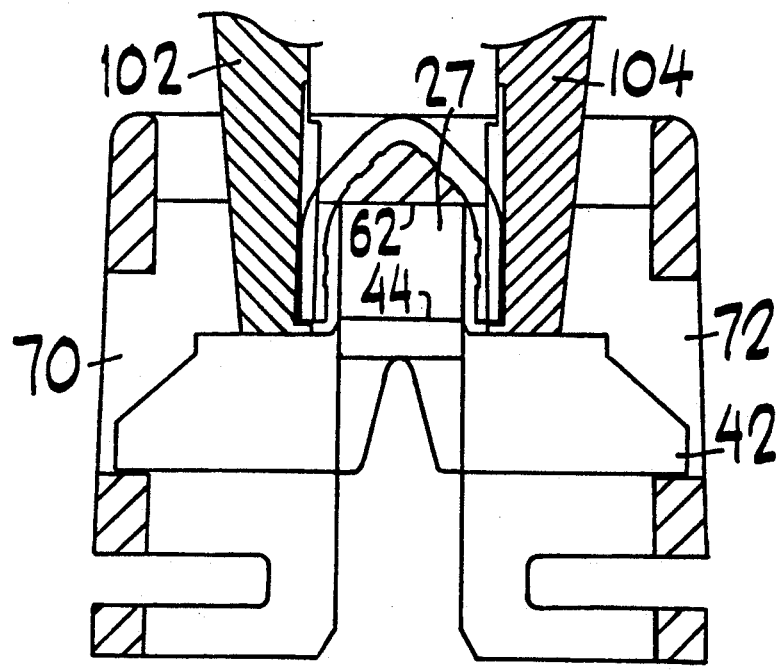
FIGS. 14(a) and (b) are similar to FIGS. 13(a) and (b) and show the clip immediately after it has been fully engaged by the applier.
Figure 14B:
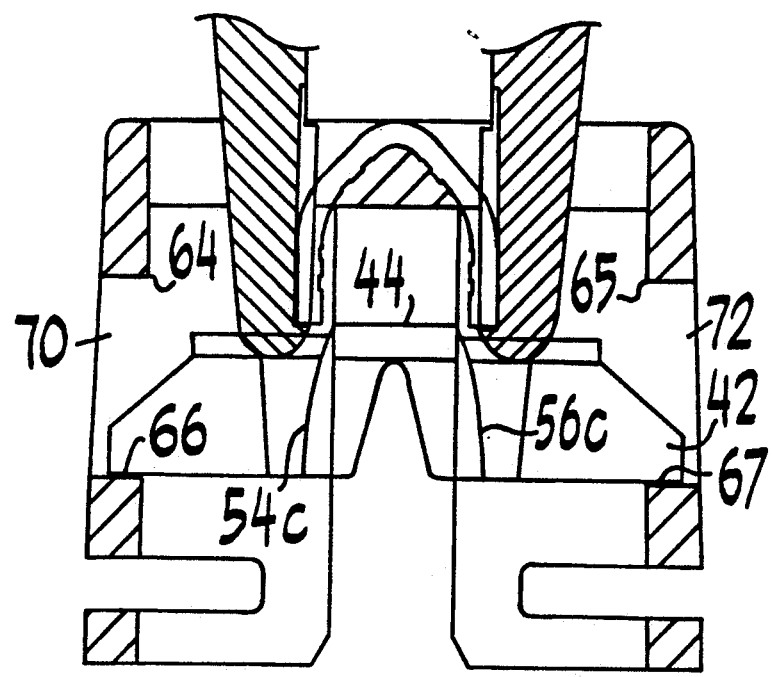
Figure 15B:
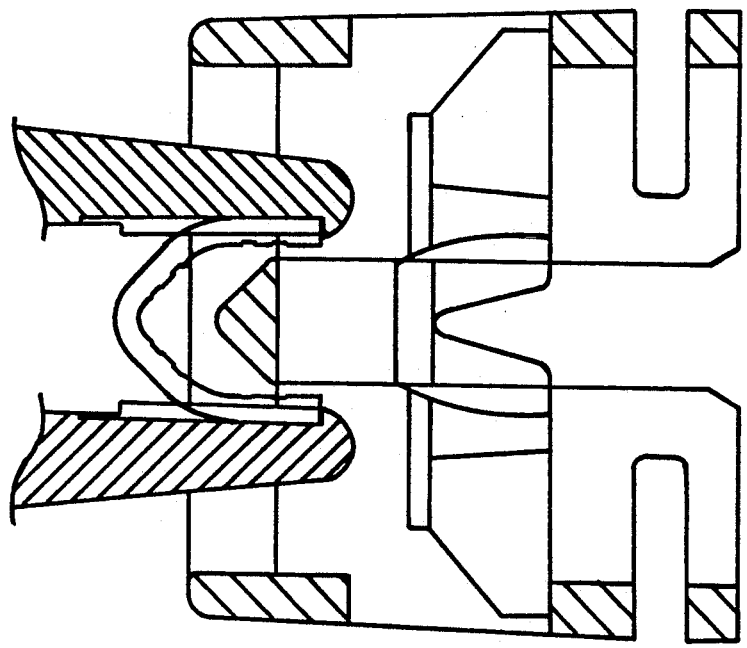
FIGS. 15(a) and (b) are similar to FIGS. 14(a) and (b) and show the clip and applier totally disengaged from the clip retainer.
Figure 15A:
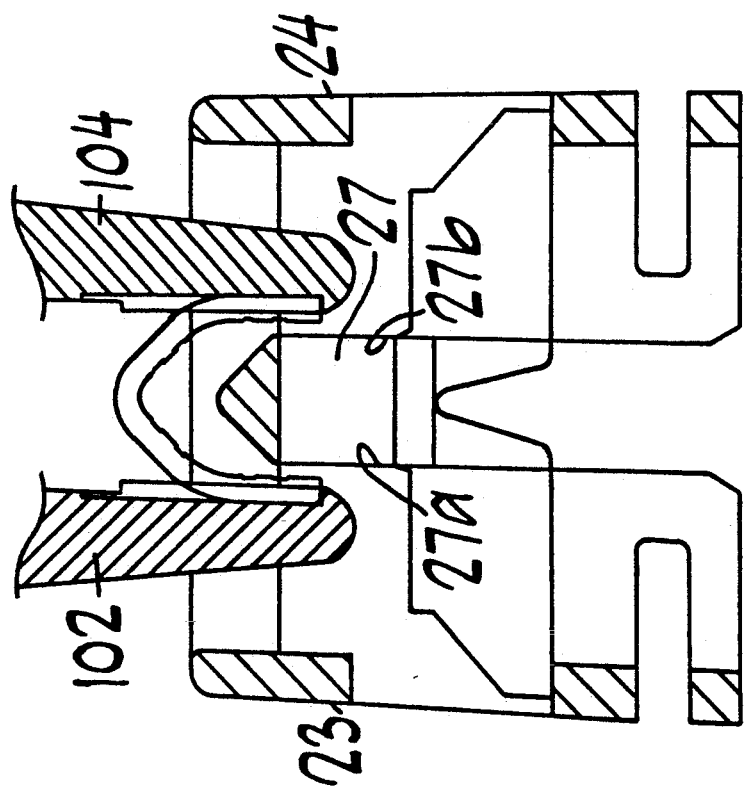

The side surface 21 of each chamber 18 faces inwardly and toward the right as seen in FIG. 1, and opposing side wall 22 is symmetrical and faces inwardly to the left into the same chamber. The top transverse edges of each wall 32 may be tapered slightly inwardly as best seen in FIGS. 1 and 3 to facilitate centering the applier jaws during clip engagement. Side surface 21 is provided with a recessed central portion 27 (best seen in FIGS. 1, 14 and 15) having vertically extending shoulders 27a and 27b which limit transverse motion of clip retainer 40 as will be understood below.

Figure 4:
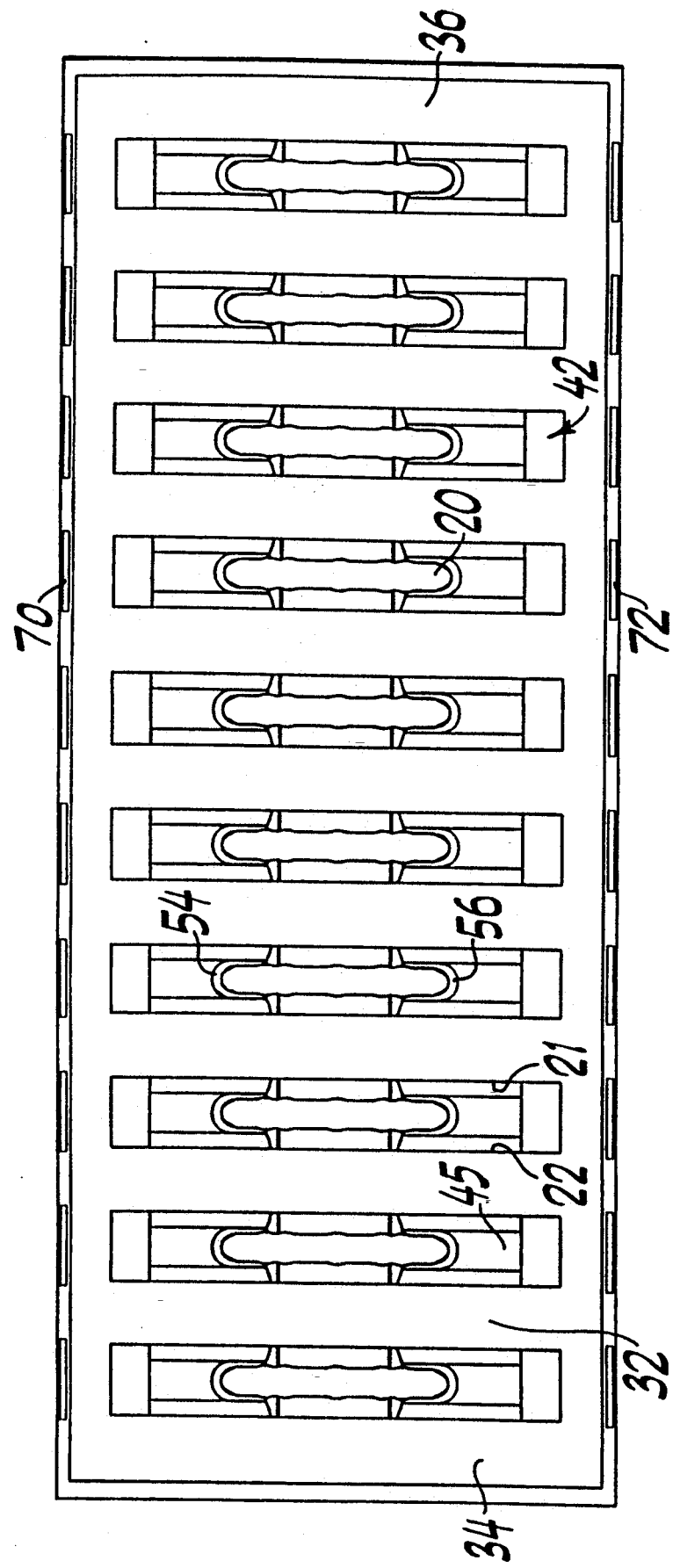
FIG. 4 is a top plan view of FIG. 3.
Figure 13B:
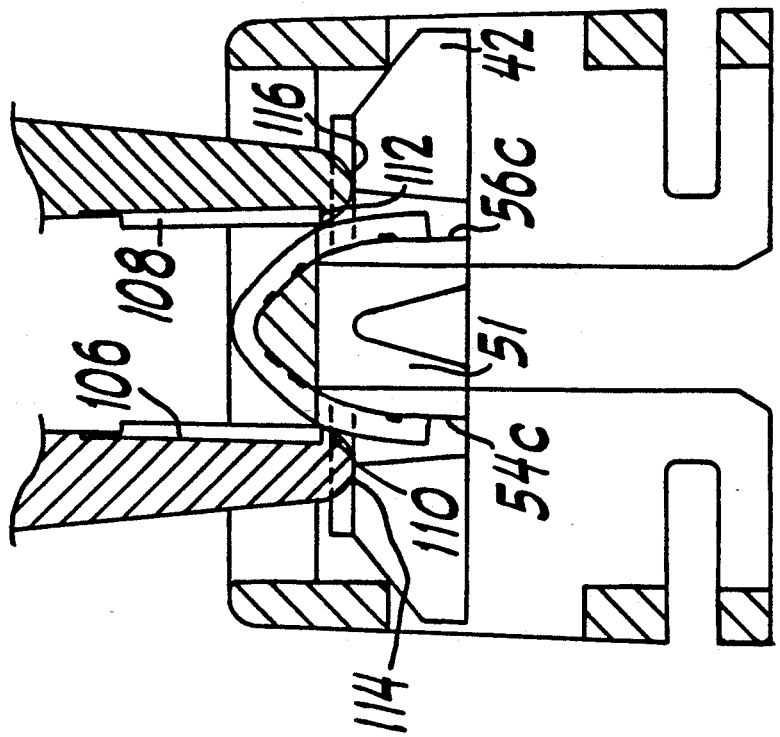
FIGS. 13(a) and (b) are diagrammatic cross-sectional elevational views of a representative clip chamber such as that shown exposed at the left side of FIG. 5. Both views 13(a) and 13(b) show the clip just prior to its being engaged by a clip applier, view (a) showing the clip retainer in elevation and view (b) showing it in cross-section.
Figure 13A:
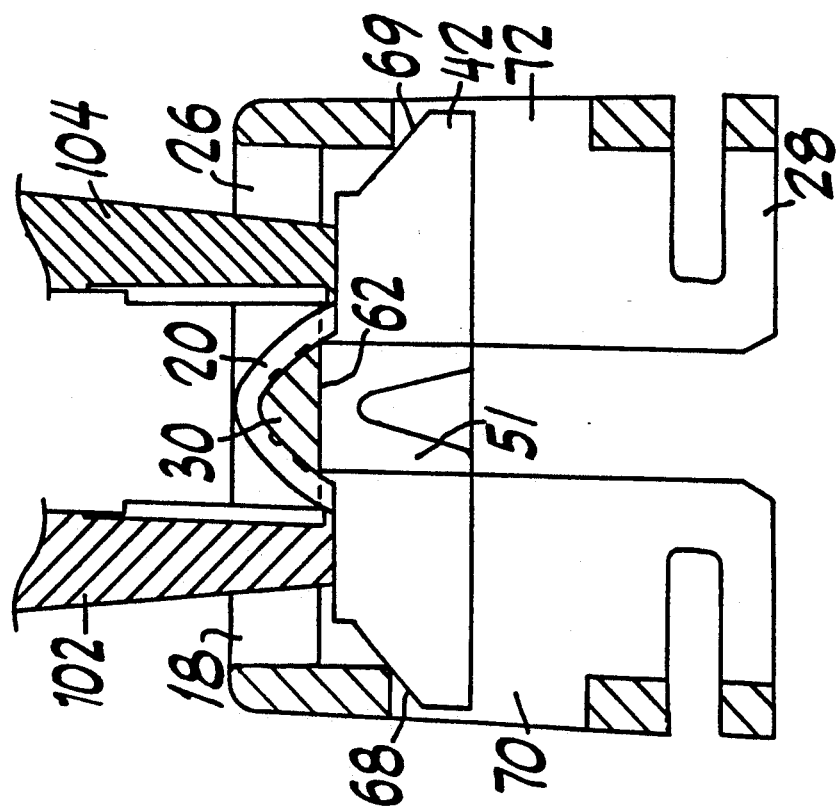

Each chamber 18 is adapted to receive a single clip retainer 40. An entire cartridge has as many retainers 40 as it has clips 20, the total obviously depending on how many clips the cartridge is desired to hold. In the preferred embodiment, each clip retainer 40 is an integral, molded block 42 (best seen in FIGS. 8-12) having top surface portions 43, 44, and 45 and bottom surface portions 46, 47 and 48. For ease of explanation, block 42 will be referred to as having symmetrical left and right halves 49 and 50 and a centrally located body portion 5 having a width slightly greater than that of halves 49 and 50. Block 42 is provided with a pair of downwardly tapering clip leg receiving bores 54 and 56 which have transversely extending clip leg engaging side surfaces 54a, 54b and 56a, 56b, respectively. In the preferred embodiment, the distance between the bottom-most portions of surfaces 54a and 54b (and between 56a and 56b) is approximate 0.002 inches less than the thickness of the clip leg designed to be received in each bore in order to provide some frictional contact. Because of the taper of bores 54 and 56 (best seen in FIG. 4) any clip received in the bores will be frictionally held only near the bottom of block 42. This creates a side wall type of frictional engagement which facilitates use of cartridge 10 with clips which may have a hydroxyapatite or other tissue gripping enhancing coating on its tissue contacting surface. The coating would generally be only on the inside surfaces of each leg and not on the lateral sides of the clip legs which contact side surfaces 54a, 54b and 56a, 56b. The lateral sides of the clip lie transversely within cartridge 10. Inner clip contacting surfaces 54c and 56c are shaped to conform to the profile of the clip designed to be received in the bore (as best seen in FIG. 13b. The transverse distance between surfaces 54c and 56c is set to be comparable to that between the opposing clip legs so that the legs will be prevented from closing but will not be significantly held by surfaces 54c and 56c.

Figure 16:
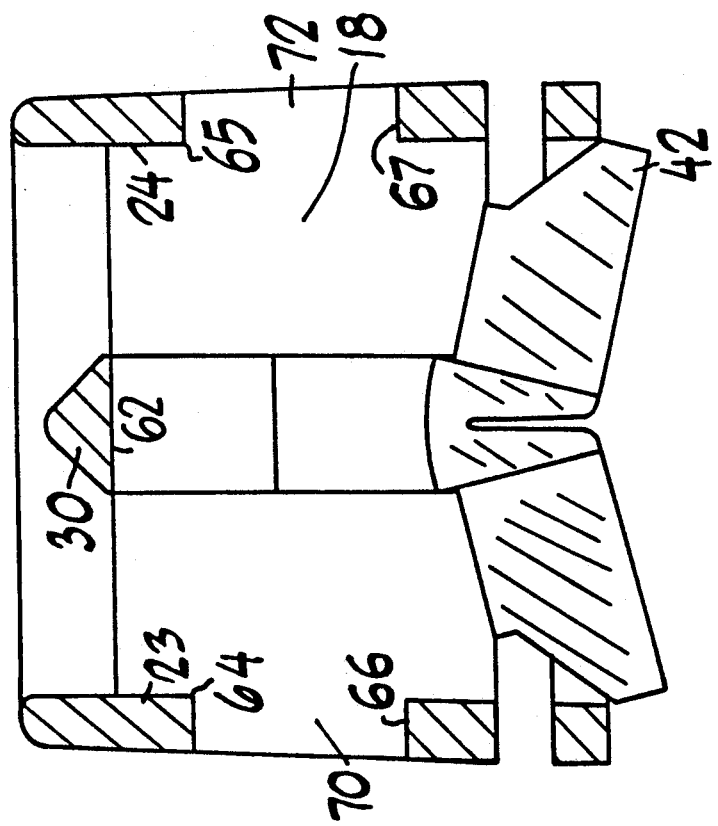
FIG. 16 is a diagrammatic cross-sectional elevational view of a single clip chamber showing a clip retainer being inserted into the bottom of the chamber.

During assembly of the components shown in FIG. 1 a single clip retainer 40 is inserted into its respective clip chamber 18 through bottom aperture 28. The central portion of each block 42 is cut-away with a notch 60 which allows the block halves 49 and 50 to be deformed sufficiently during the assembly process to allow the greater block length A (best seen in FIG. 7) to pass through the smaller opening B in the bottom aperture 28 of each clip chamber. A diagrammatic representation of this assembly process is shown in FIG. 16. Once in chamber 18, block 42 will straighten out and be free to move vertically over a certain range of motion. At its top-most limit, central portion 44 of block 42 will contact the bottom surface 62 of post 30 while inner edges 64 and 65 of the top portions of side walls 23 and 24, respectively, will contact the angled side walls 68 and 69. The bottom-most limit is set by retainer support ledges 66 and 67. In the preferred embodiment, top and bottom limits 64, 66 and 65, 67 are defined by apertures 70 and 72 formed in the longitudinally extending side walls 23 and 24 of each chamber 18.

It will be understood that a loaded clip cartridge comprises a unitary cartridge body 12, a plurality of clips 20 and a corresponding plurality of retaining members 40. When loaded with clips, the individual components of cartridge 10 are all held together firmly. When a clip is removed from a chamber 18 (as will be explained below), the corresponding retaining block 42 will be separated from its respective clip and will be able to freely move within its chamber 18 between the aforementioned top and bottom limits.

The manner in which a clip is engaged by a clip applier is best understood by reference to FIGS. 5, 6, 13, 14 and 15. A representative manual clip applier 100 is shown in position to engage a clip 20 in a chosen clip chamber 18. Applier 100 has a pair of jaws 102 and 104 at its distal tip, the jaws provided with a groove 106 and 108, respectively and corresponding end-dams 110 and 112. As the applier jaws 102 and 104 are first introduced into chamber 18, the transverse tapered edges of top surface 32 assist in centering the applier over clip 20. As the jaws are further inserted into chamber 18, the distal tips 114 and 116 of the jaws are further centered over clip 20 by transversely extending tapered ramps 57a, 58a and 57b and 58b situated on top surfaces 43 and 45 of block 42. When fully seated between the ramps on the top surface of block 42, the end-dams 110 and 112 will, as best seen in FIG. 13b, be touching surfaces 43, 45 and the outer surfaces of the clip legs. Further downward motion of jaws 102 and 104 will, as best seen in FIGS. 14a and 14b, compress the clip legs into a generally parallel configuration since (as best seen in FIG. 14b) the distal tips of the jaws have pushed block 42 and, consequently, clip leg supporting surfaces 54c, 56c, out of the way so they cannot engage the interior surfaces of the clip legs. The curved profile of surfaces 54c and 56c enables the clip legs to be compressed inwardly as block 42 is forced downwardly by the jaws. While FIG. 13b appears to show surfaces 54c and 56c in contact with the inside surfaces of the clip legs, this need not be the case since, as stated above, the primary frictional contact between block 42 and its clip is along side surfaces 54a, 54b and 56a, 56b. When block 42 has been pushed downwardly a sufficient distance, end-dams 110 and 112 will pass beyond the ends of the clip legs and, because of the inherent resiliency in the metallic clip, the clip legs will expand slightly into grooves 106 and 108 thereby placing the ends of the clip legs proximally of end-dams 110 and 112. It should be understood that cartridge 10 will also operate with appliers not having end-dams. The height of windows 70, 72 (i.e. the vertical distance between top and bottom limits 64, 66 and 65, 67) must be adjusted for each clip size such that in the top-most position of block 42 its central surface 44 is in (or near) abutment with the bottom surface 62 of post 30 when the inclined surfaces 68 and 69 of block 42 are in engagement with top limits 64 and 65. Similarly, the bottom limits 66 and 67 must be sufficiently spaced from the top limits such that block 42 may be pushed downwardly enough to enable the end-dams to pass beyond the end of the clip leg.

It will be understood that at this point block 4 is free to move within chamber 18. Block 42 is prevented from transversely moving within chamber 18, and therefore prevented from becoming totally disengaged from cartridge 10 by the interaction between the enlarged central body portion 51 of block 42 and the corresponding recess 27 formed in side walls 21 and 22. Body portion 51 and shoulders 27a and 27b keep block 42 within chamber 18 while enabling it to ride within recess 27.

Figure 18:
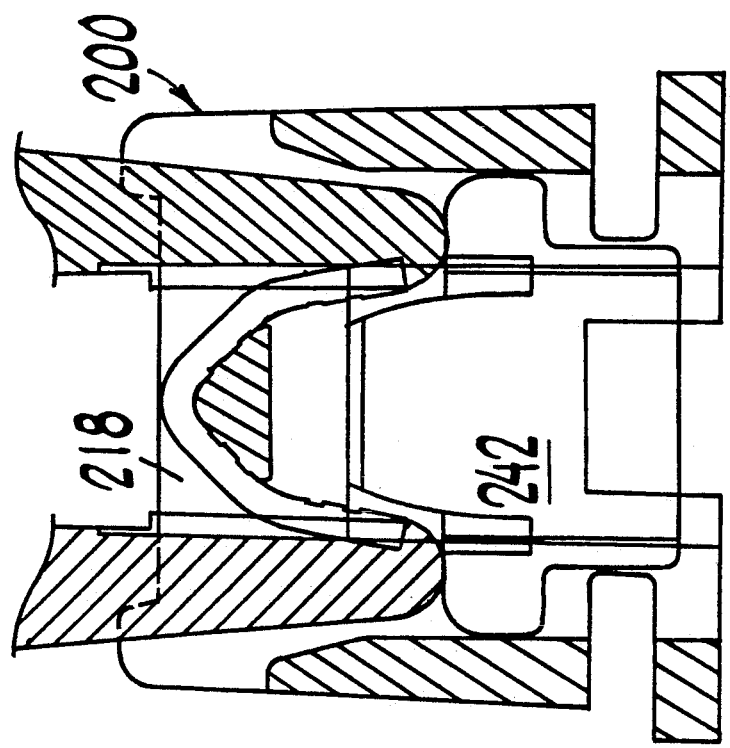
FIG. 18 is a view of FIG. 17 after the clip applier has engaged the clip.
Figure 17:
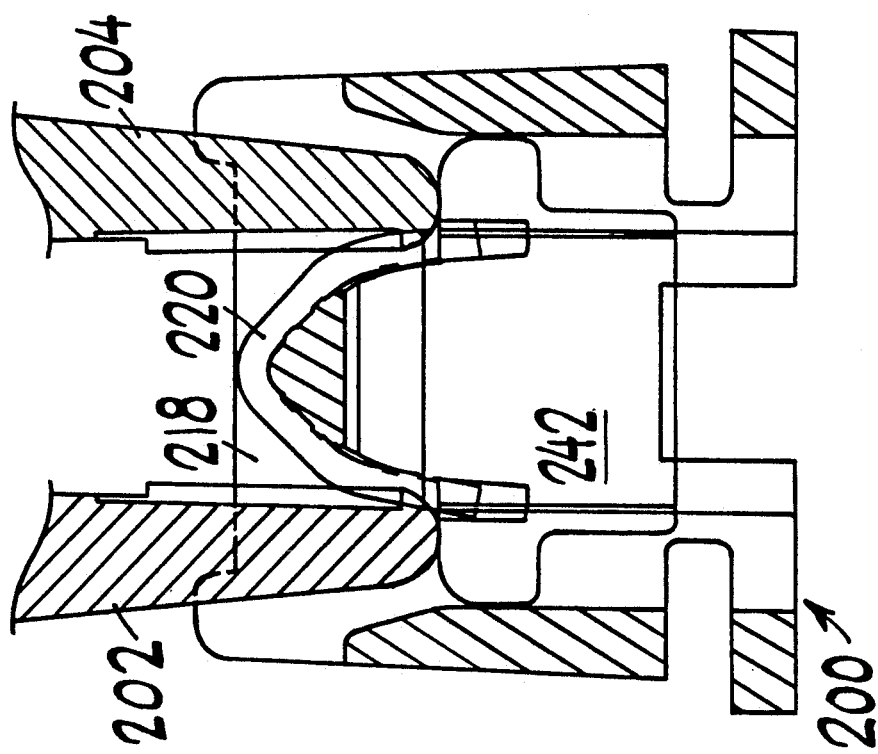
FIG. 17 is an assembled, cross-sectional elevational view of a first alternate embodiment of the invention showing the clip being supported by a clip retainer.

A first alternate embodiment of the invention is shown in FIGS. 17 and 18 and is generally designated as cartridge 200 having clip retaining member 242 in each chamber 218. The primary difference between this first alternative and the preferred embodiment is the shape of retaining member 242 and the manner in which it may be retained within its individual clip chamber 218. Any suitable means (not shown) may be used to keep member 242 from falling out of chamber 218 after the clip 220 has been engaged by applier jaws 202, 204.

Figure 20:
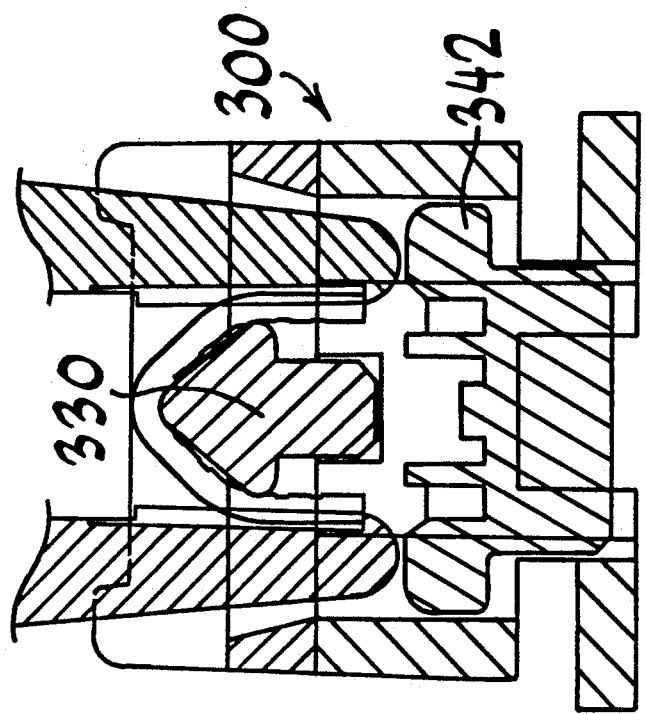
FIG. 20 is a view of FIG. 19 after the clip applier has engaged the clip.
Figure 19:
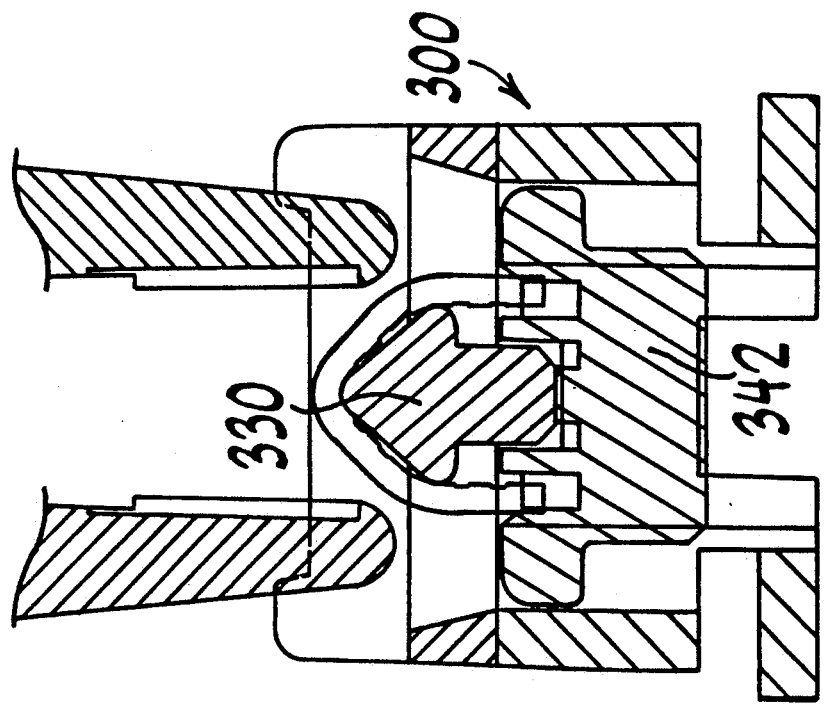
FIG. 19 is an assembled, cross-sectional elevational view of a second alternate embodiment of the invention showing the clip being supported by a clip retainer.
Figure 21:
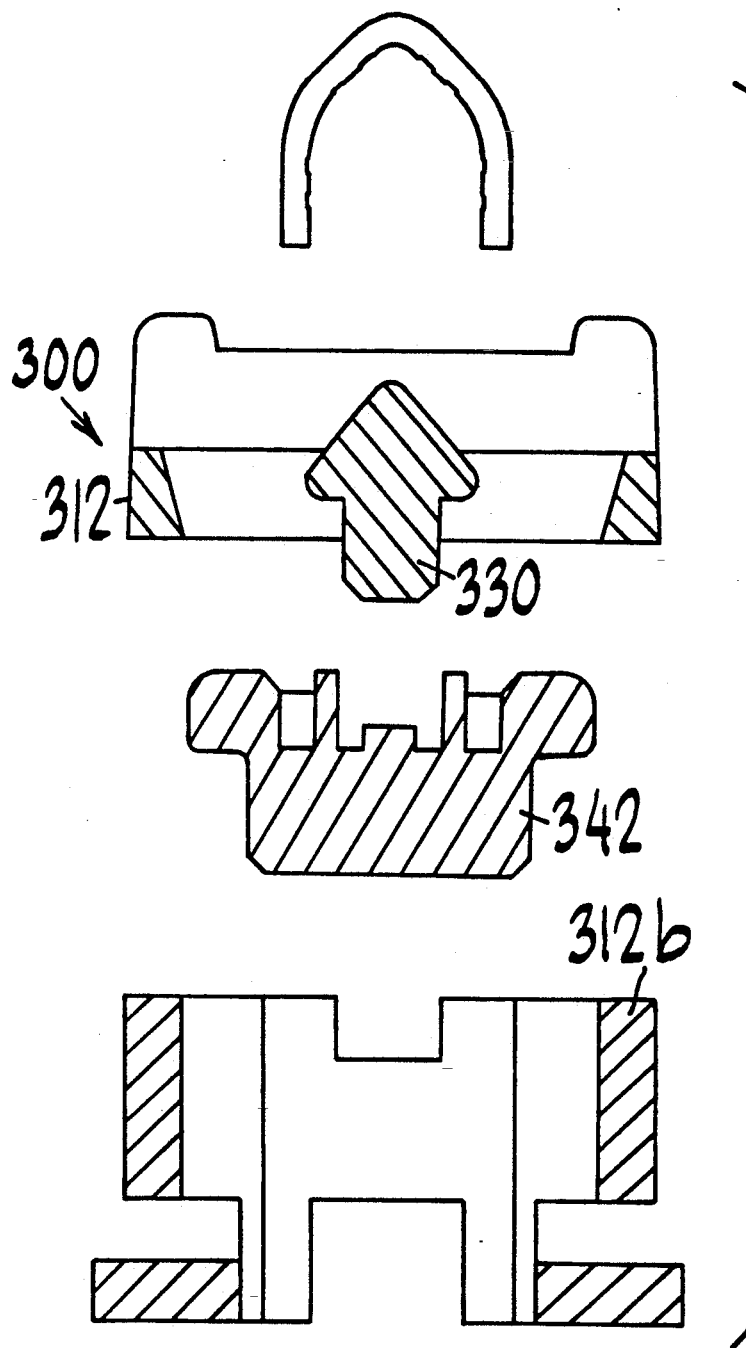
FIG. 21 is an exploded view of FIG. 19.

A second alternate embodiment is shown in FIGS. 19, 20 and 21 and is generally designated as clip cartridge 300 having clip retaining member 342. While similar in operation to the preferred embodiment, cartridge 300 employs differently shaped components. Additionally, the body of cartridge 300 is formed in two halves 312(a) and 312(b) which are shown in exploded form in FIG. 21. It will be understood that central support post 330 is integrally formed with top cartridge half 312a and, when assembled, clip retainers 342 will be captured between cartridge halves 312a and 213b.

Figure 23:
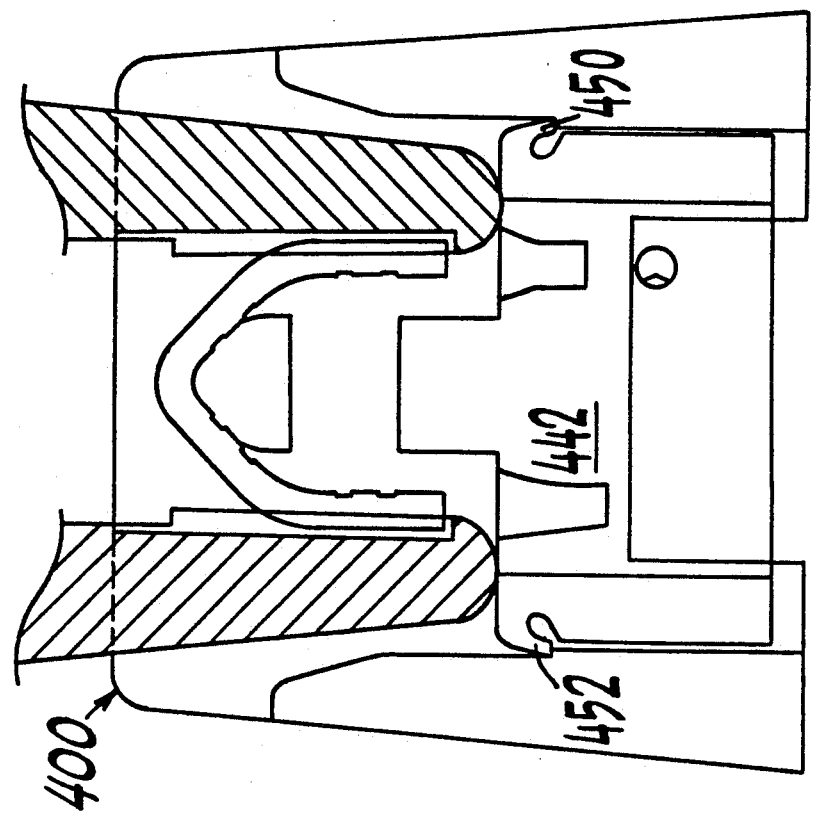
FIG. 23 is a view of FIG. 22 after the clip applier has engaged the clip.
Figure 22:
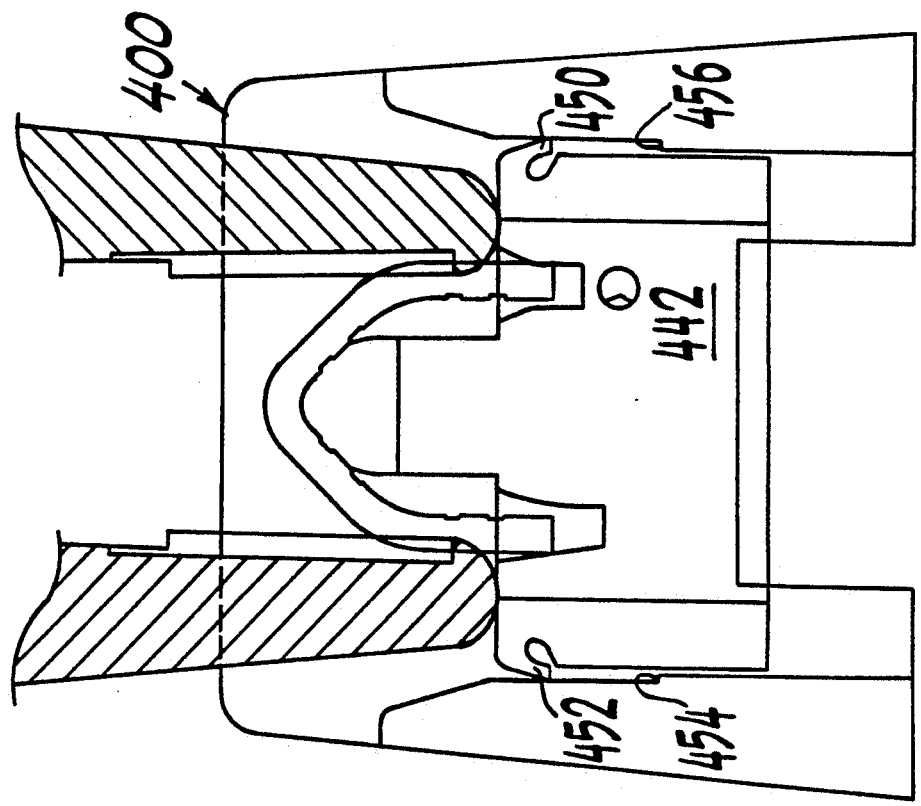
FIG. 22 is an assembled, cross-sectional elevational view of a third alternate embodiment of the invention showing the clip being supported by a clip retainer.

A third alternate embodiment is shown in FIGS. 22 and 23 and is generally designated as cartridge 400 having clip retaining member 442. While similar in operation to the preferred embodiment, cartridge 400 utilizes a pair of resilient tabs 450 and 452 in cooperation with ledge surfaces 454 and 456 in order to keep retainer 442 from becoming dislodged from cartridge 400.

Figures 24, 25:
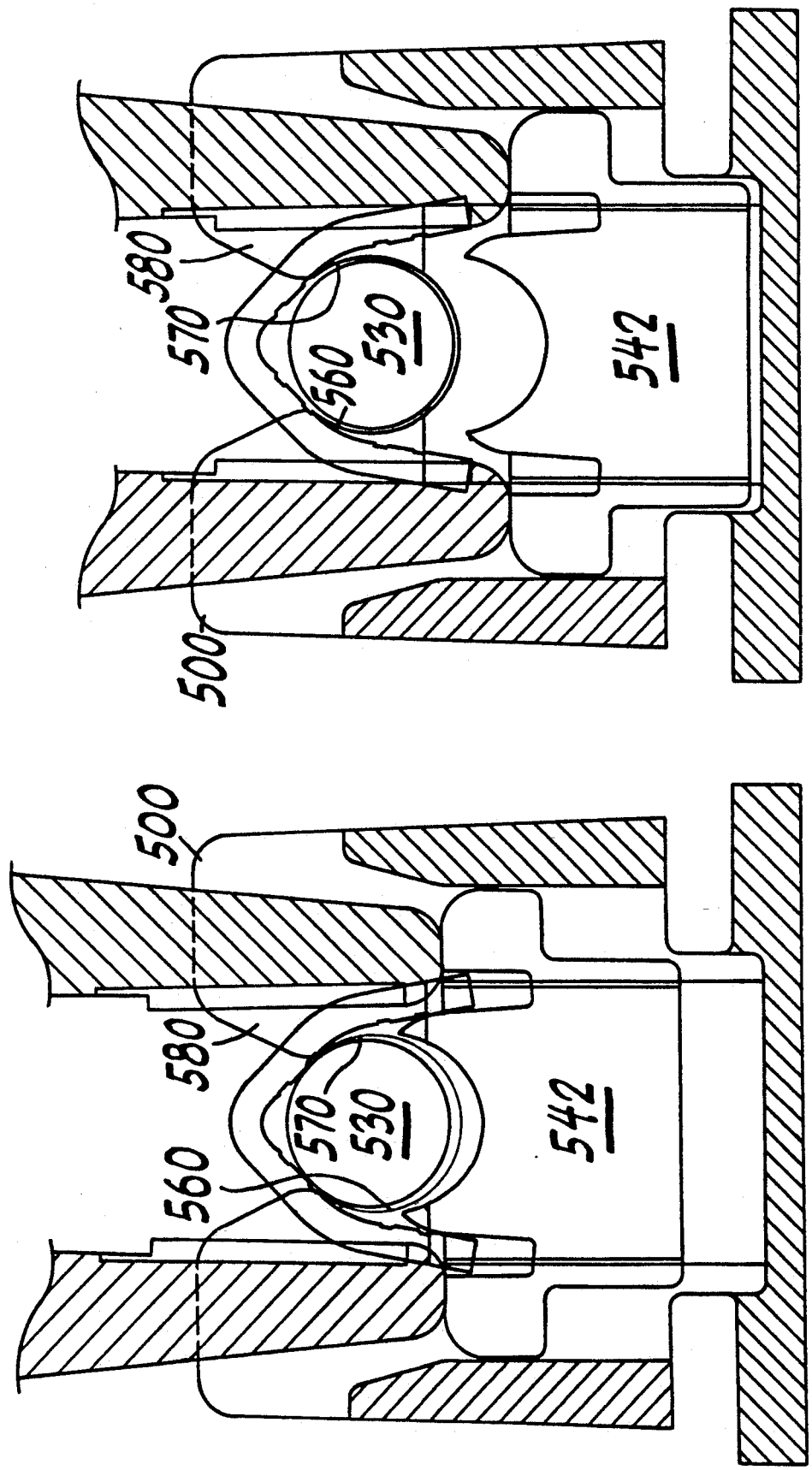
FIG. 24 is an assembled, cross-sectional elevational view of a fourth alternate embodiment of the invention showing the clip being supported by a clip retainer.
FIG. 25 is a view of FIG. 24 after the clip applier has engaged the clip.

A fourth alternate embodiment is shown in FIGS. 24 and 25 and is generally designated as cartridge 500 having clip retaining member 542. As with the previous alternate embodiments, cartridge 500 operates in a similar manner but differs in the way in which clip retainer 552 is retained within the cartridge. In this embodiment the retaining member 542 may be inserted from the top and, therefore, the bottom surface of cartridge 500 may be closed. After member 542 is inserted, center post 530 may be pressed into place above it and held there by the cooperative action of inwardly facing curved surfaces 560 and 570 in each transverse wall 580. Post 530 is part of a longitudinally extending piece containing individual posts in each chamber (similar to the concept shown in FIG. 31).

Figure 26:
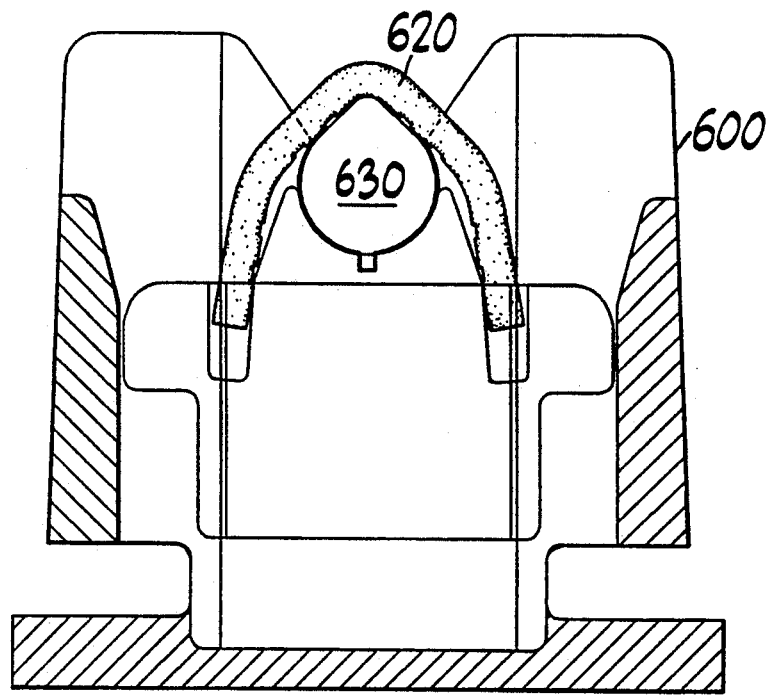
FIG. 26 is an assembled, cross-sectional elevational view of a fifth alternate embodiment of the invention showing the clip being supported by a clip retainer.

A variation of this embodiment is shown in FIG. 26 and is designated cartridge 600 having a central post 630 shaped to better conform to the hinge point of clip 620.

Figure 28:
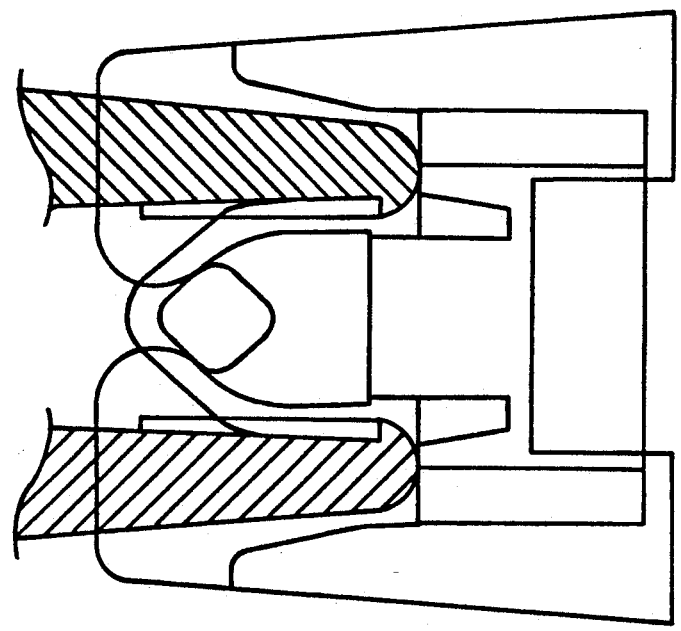
FIG. 28 is a view of FIG. 27 after the clip applier has engaged the clip.
Figure 27:
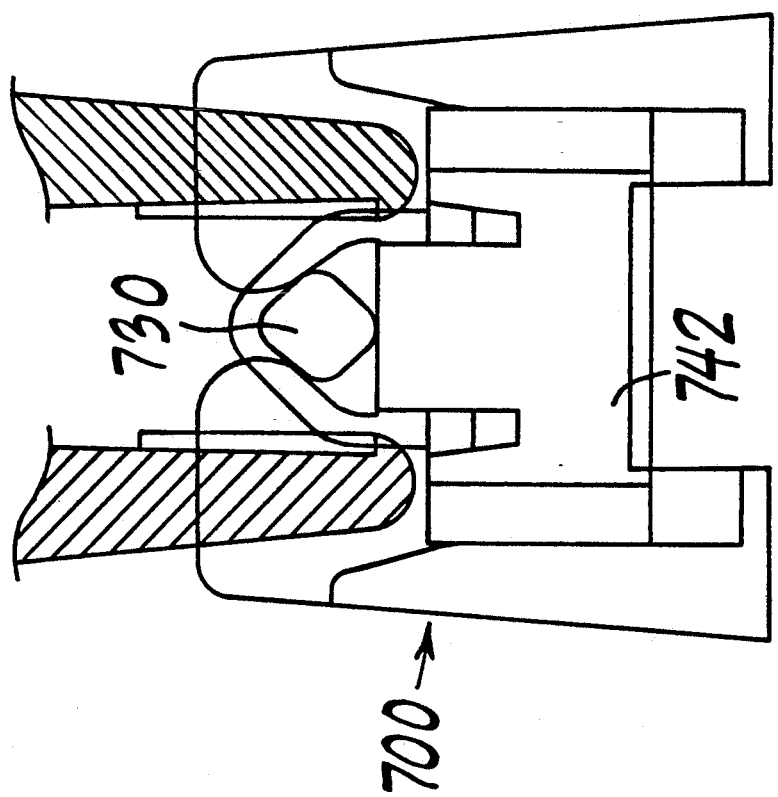
FIG. 27 is an assembled, cross-sectional elevational view of a sixth alternate embodiment of the invention showing the clip being supported by a clip retainer.

Other alternative embodiments could be produced in which the clip retainer is otherwise attached to a central support post. For example, the retainer could be integrally molded with the post and designed to breakaway from the post. Such a alternative is shown in FIGS. 27 and 28 wherein the cartridge is designated 700 and the retainer is 742.

Figure 30:
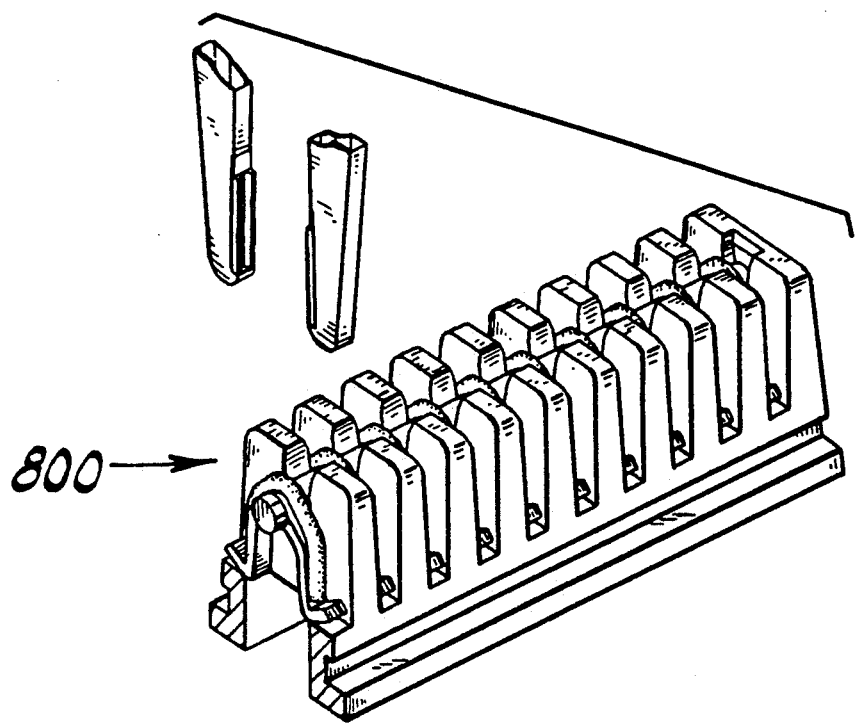
FIG. 30 is an assembled view of FIG. 29 showing the clip applier in place to engage a clip.
Figure 29:
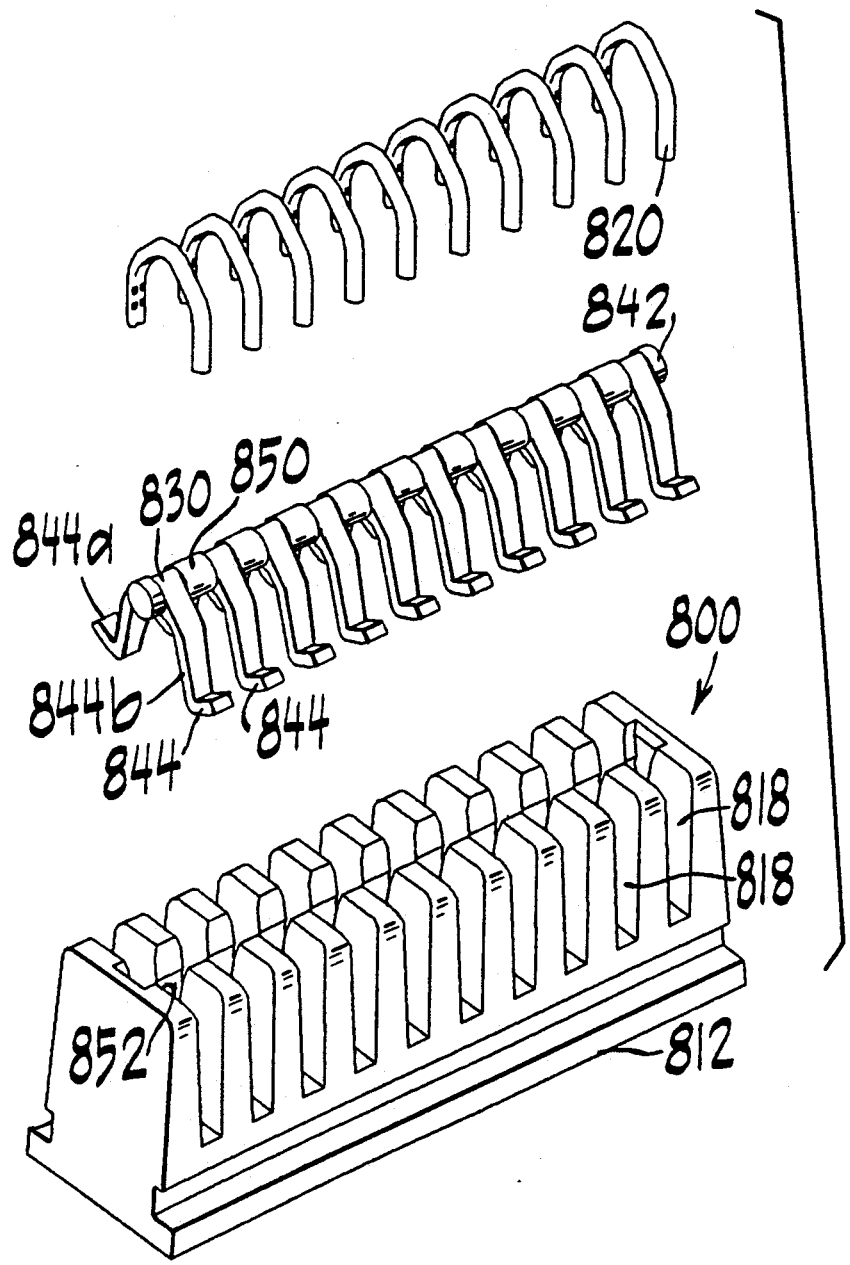
FIG. 29 is an exploded front perspective view of a seventh alternate embodiment of the invention showing the clip being supported by a clip retainer.

Another alternative could be envisioned where the clip retainers are all molded together as one unit which fits into a clip body. For example, FIGS. 29 and 30 show a cartridge 800 having a clip retainer 842. Retainer 842, as best seen in FIG. 29, may be molded in one integral piece having individual retaining portions 844 adapted to fit into each chamber 818. Portions 844 have legs 844a and 844b adapted to support the inside of the legs of clip 820 (best seen in FIGS. 30 and 32). Post portions 830 are interposed between legs 844a and 844b, and circular bushing portions 850 separate adjacent retaining portions 844. An interlocking fit between bushings 850 and complementarily shaped recesses 852 (similar to surfaces 560 and 570 in FIGS. 24 and 25) keeps retaining member 842 connected to the body portion 812 of cartridge 800. (Alternately, the legs could be designed to break or give after a certain amount of inward motion.) After the clip is loaded into chamber 818 the natural resiliency of legs 844a and 844b keeps them outwardly biased to hold clip 820 (best seen in FIGS. 31 and 32). Applier jaws 802 and 804 disengage legs 844a and 844b by pushing them inwardly as best seen in FIG. 33. The interaction between the ends of legs 844a and 844b with the inside surfaces of recess 860 keeps them from resisting withdrawal of the clip from chamber 818. It will be understood that the embodiment of FIGS. 29-33 retain each clip within its chamber primarily by frictional engagement between the insides of the clip legs and the outside of the retainer legs. The clip is released by laterally moving these surfaces from each other rather than downwardly moving the clip retaining members of the previously described embodiments.

It should be understood that virtually any clip applier will be suitable for use with cartridge 10 or any of the alternate embodiments provided it is operable with the particular clip loaded into the cartridge. Consequently, the invention provides a clip cartridge usable with appliers having end-dams as well as appliers not having end-dams.

Figure 34:
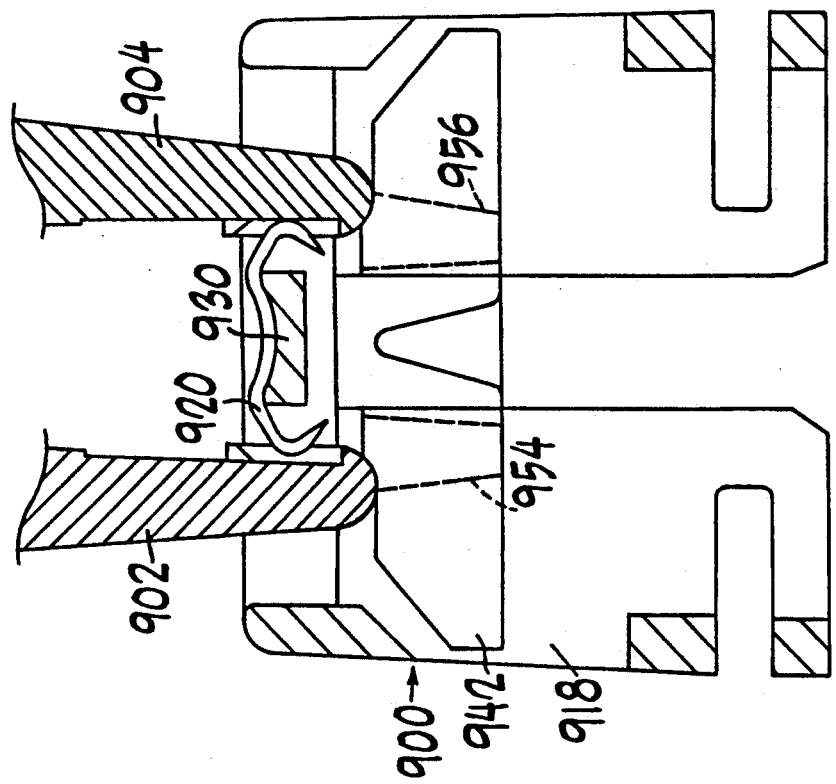
FIG. 34 is an assembled, cross-sectional elevational view of an embodiment of the invention for use with a surgical staple, the position of the retaining member in this view being shown displaced by the jaws of an applier.

Adapting the invention to particularly shaped staples (such as that shown in the aforementioned U.S. patent to Giersch et al.) will be understood by those skilled in the art to require minor modifications to the retaining blocks 42, etc. Since the frictional engagement between the block and the staple is along the lateral sides of the staple, a simple change in the shape of the leg receiving bores is all that is necessary to adapt cartridge 10 to such a staple. For example, FIG. 34 shows a staple cartridge embodiment 900 essentially identical to cartridge 10 except for the post 930, block 942 and bores 954 and 956 (shown only roughly in phantom). It will be understood that the post conforms to the profile of staple 920 and the bores are sized to receive the legs of the staple and to frictionally engage the sides of the legs.

Details of staple 920 may be obtained by reference to the aforementioned Giersch et al. patent. Applier jaws 902 and 904 are similar to other appliers disclosed herein, but are adapted to receive staple 920 and to push block 942 downwardly. FIG. 34 shows block 942 already displaced below staple 920 and it will be noted that block 942 normally sits higher in chamber 918 when it is in engagement with staple 920.

It will be understood by those skilled in the art that numerous other modifications and improvements may be made to the preferred embodiment of the invention disclosed herein without departing from the spirit and scope thereof.

What is claimed is:

1. A cartridge for retaining a plurality of hemostatic clips, each clip having a pair of legs extending in the same general direction from a hinge point to form a C-shape and adapted to be removed from said cartridge by a forceps-type clip applier, said cartridge comprising:
   a body having a plurality of clip compartments;
   a clip hinge support member secured within each compartment, each said support member adapted to prevent downward motion of a clip by supporting said clip adjacent its hinge point;
   a clip-retaining member situated in each compartment so as to be between the legs of a clip to be placed in said compartment;
   means for holding each said clip-retaining member in a first predetermined position where it will be adjacent a clip to be placed in its compartment;
   means for enabling each said clip-retaining member to be entirely displaced away from a clip to be placed in said compartment by a clip applier inserted into that clip's compartment thereby moving each said clip-retaining means from its said first predetermined position to a second predetermined position where it will be spaced from the clip that was placed in said compartment.

2. A cartridge according to claim 1 wherein all of said clip retaining members associated with said cartridge are integrally formed together.

3. A cartridge according to claim 1 wherein each said clip-retaining member substantially prevents the legs of a clip from moving toward each other as the clip is being engaged by a clip applier.

4. A cartridge according to claim 3 further comprising means on each said clip-retaining member which enable it to engage a clip applier so that each said clip-retaining member may be moved away from said clip hinge support member by the clip applier while the clip applier is being moved into engagement with a clip.

5. A cartridge according to claim 3 for use with a forceps-type clip applier having a pair of jaws for receiving a clip, each jaw having a groove for receiving a clip leg, said groove abutting a distal end-dam for limiting distal movement of the end of a clip leg received in said groove, said clip-retaining member for supporting the legs of a clip during engagement thereof by the end-dam on each jaw.

6. A cartridge according to claim 1 further comprising prevention means to prevent each said clip-retaining member from becoming dislodged from its respective clip compartment.

7. A cartridge according to claim 6 wherein said prevention means is operative after the clip supported by a clip-retaining member has been removed from its respective clip compartment.

8. A cartridge for retaining a plurality of hemostatic clips, each clip having a pair of legs extending in the same general direction from a hinge point to form a C-shape and adapted to be removed from said cartridge by a forceps-type clip applier, said cartridge comprising:
   a body having a plurality of clip compartments;
   a clip hinge support member secured within each compartment, each said support member adapted to prevent downward motion of a clip by supporting said clip adjacent its hinge point;
   a clip-retaining member situated in each compartment so as to be between the legs of a clip to be placed in said compartment and adapted to be entirely displaced away from said clip legs by a clip applier inserted into said each compartment.

9. A cartridge according to claim 8 wherein said clip hinge support and said clip-retaining member are integrally formed together as a unit insertable into a respective clip compartment.

10. A cartridge according to claim 9 wherein all clip hinge supports and clip-retaining members associated with the cartridge are integrally formed together.

11. A cartridge for retaining a plurality of hemostatic clips, each clip having a pair of legs extending in the same general direction from a hinge point to form a C-shape and adapted to be removed from said cartridge by a forceps-type clip applier, said cartridge comprising:
   a body having a plurality of clip compartments;
   a clip hinge support member secured within each compartment, each said support member adapted to prevent downward motion of a clip by supporting said clip adjacent its hinge point;
   a clip-retaining member situated in each compartment so as to be between the legs of a clip to be placed in said compartment and adapted to prevent said legs from being moved toward each other more than a predetermined amount and further adapted to be entirely displaced away from said clip by a clip applier inserted into said each compartment.

12. A method of retaining within a clip cartridge a C-shaped clip having a pair of legs extending in the same general direction from a hinge portion comprising the steps of:
   providing a clip cartridge having a plurality of chambers for retaining clips, each chamber having a clip-supporting member adapted to support a clip adjacent its hinge portion;
   providing a separable clip-retaining member within each chamber, said clip-retaining member situated so as to be between the legs of a clip to be placed in each chamber and being separable from the clip to be retained in its respective chamber while the clip is supported by said clip-supporting member;
   securing each said clip-retaining member in its respective chamber;
   placing a clip into each said chamber.

13. A method according to claim 12 further comprising the steps of:
   providing a forceps-type clip applier having a pair of jaws at its distal tip, said jaws adapted to engage a selected one of said clips;
   placing said jaws over said selected clip and pushing said jaws downwardly onto said selected clip;
   displacing said clip-retaining member associated with said selected clip out of engagement with said selected clip;
   engaging said selected clip with said jaws;
   removing said selected clip from said cartridge.

* * * * *